United States Patent [19]

Benes et al.

[11] Patent Number: 5,639,469

[45] Date of Patent: Jun. 17, 1997

[54] TRANSMUCOSAL DELIVERY SYSTEM

[75] Inventors: Luce R. M. Benes, Saint Jean de Braye; Francoise L. R. B. Horriere, Angerville, both of France

[73] Assignee: Minnesota Mining and Manufacturing Company, St. Paul, Minn.

[21] Appl. No.: 259,873

[22] Filed: Jun. 15, 1994

[51] Int. Cl.$^6$ .................................................. A61F 13/00
[52] U.S. Cl. .......................... 424/435; 424/434; 424/447; 424/448; 424/449
[58] Field of Search .................................... 424/447, 449, 424/443, 434, 435, 448; 514/947, 56, 54

[56] References Cited

U.S. PATENT DOCUMENTS

| | | | |
|---|---|---|---|
| 3,972,995 | 8/1976 | Tsuk et al. | 424/28 |
| 4,615,697 | 10/1986 | Robinson | 604/890 |
| 4,699,900 | 10/1987 | Bayol et al. | 514/54 |
| 4,713,373 | 12/1987 | Bayol et al. | 514/54 |
| 4,849,224 | 7/1989 | Chang et al. | 424/434 |
| 4,963,367 | 10/1990 | Ecanow | 424/485 |
| 4,990,502 | 2/1991 | Lormeau et al. | 514/56 |
| 5,013,724 | 5/1991 | Petitou et al. | 514/54 |
| 5,084,564 | 1/1992 | Vila et al. | 536/21 |
| 5,110,918 | 5/1992 | Casu et al. | 536/21 |
| 5,113,860 | 5/1992 | McQuinn | 128/632 |
| 5,273,757 | 12/1993 | Jaeger et al. | 424/448 |
| 5,346,701 | 9/1994 | Heiber et al. | 424/435 |

FOREIGN PATENT DOCUMENTS

| | | |
|---|---|---|
| 0130550 | 1/1985 | European Pat. Off. . |
| 0283434 | 9/1988 | European Pat. Off. . |
| 91/06290 | 5/1991 | WIPO . |
| 92/11294 | 7/1992 | WIPO . |
| 93/19737 | 10/1993 | WIPO . |

OTHER PUBLICATIONS

*Biochem. Biophys. Res. Commun.* 1983, 116, 492–499 (Choay et al.).

*Proceed. Intern. Symp. Control. Rel. Bioact. Mater.* 1992, 19, 409–410 (Yang et al.).

*Proceed Intern. Symp. Control. Rel. Bioact. Mater.* 1992, 19, 514–515 (Santiago et al.).

*Quarterly Journal of Medicine*, New Series 83, Apr. 1992, 300, 259–282 (Kanabrocki et al.).

*International Journal of Pharmaceutics* 1992, 82, 171–177 (Bonina et al.).

*American Journal of Medicine*, Sep. 1964, 37, 408–416 (Windsor et al.).

*Primary Examiner*—Paul R. Michl
*Assistant Examiner*—Sharon Howard
*Attorney, Agent, or Firm*—Gary L. Griswold; Walter N. Kirn; Ted K. Ringsred

[57] ABSTRACT

A device for delivering a heparinic anticoagulant across a mucosal surface in order to achieve or maintain a therapeutically effective blood level of the heparinic anticoagulant. The device involves a matrix containing a therapeutically effective amount of a heparinic anticoagulant, and a mucoadhesive or other mechanism for maintaining the matrix in contact with the mucosal surface for a time sufficient to allow release of the heparinic anticoagulant to the mucosal surface.

16 Claims, 1 Drawing Sheet

TRANSMUCOSAL DELIVERY SYSTEM

BACKGROUND OF THE INVENTION

1. Field of the Invention

This invention relates to transmucosal drug delivery systems. In another aspect this invention relates to drug delivery systems containing a heparinic anticoagulant, such as a heparin or a heparin fragment.

2. Description of the Related Art

Transmucosal drug delivery systems are designed to deliver a therapeutically effective amount of drug across a mucosal surface, typically the oral mucosa, of a patient. Delivery of drugs across the oral mucosa avoids hepatic first-pass inactivation, poor or erratic absorption from the gastro-intestinal tract, inactivation by gastro-intestinal fluids, and other modes of inactivation characteristic of oral drug ingestion. Sustained release adhesive bandages, patches, and the like that contain drugs are known to the art.

Patent Application WO 90/06505 (Scholz et al.) discloses a bioadhesive composition comprising drug and a particulate polymeric resin dispersed in a hydrophobic elastomeric component. CARBOPOL™ resins are among the polymeric resins said to be suitable and the hydrophobic resin can be a mixture of VISTANEX™ L100 polyisobutylene and VISTANEX LMMH polyisobutylene.

Heparin is an anionic polysaccharide of mammalian origin having anticoagulant properties. It is a heterogeneous mixture of variably sulfated polysaccharide chains composed of repeating units of D-glucosamine and either L-iduronic or D-glucuronic acids. The molecular weight ranges from 6,000 to 30,000 daltons. Heparin is strongly acidic because of its content of covalently linked sulfate and carboxylic acid groups. In heparin sodium, the acid protons of the sulfate units are partially replaced by sodium ions. Heparin is biosynthesized and stored in mast cells of various animal tissues, particularly liver, lung or gut. Commercial heparin is isolated from beef lung or pork intestinal mucosa. Heparin is given parenterally for the treatment and prophylaxis of thrombo-embolic disorders and as an adjunct to thrombolytic therapy.

Low molecular weight (1500–8000 daltons) heparins are fragments of heparin with anticoagulant activity. They can be obtained by chemical or enzymatic depolymerization of standard heparin. Commercially available low molecular weight heparins differ in their method of production, molecular weight range, chain end groups and degree of sulfation. Like heparin, these compounds inhibit the action of antithrombin III but they are characterized by a higher ratio of anti-factor-Xa to anti-thrombin activity than heparin. Low molecular weight heparins have less effect on platelet aggregation than heparin. They are used in the treatment and prophylaxis of venous thromboembolism. Therapy may be monitored by measurement of plasma anti-factor-Xa activity.

Dalteparin sodium is prepared by the nitrous acid degradation of heparin obtained from the intestinal mucosa of pigs. The majority of the components have a 6-O-sulpho-2, 5-anhydro-D-mannitol structure at the reducing end of the chain. The molecular weight of 90% of the components is between 2000 and 9000 daltons and the average molecular weight is about 5000 daltons. The sulfur content is about 11%.

Enoxaparin sodium is prepared by alkaline degradation of heparin benzyl ester obtained from the intestinal mucosa of pigs. The majority of the components have a 2-O-sulfo-4-enepyranosuronic acid structure at the non-reducing end and a 2-N,6-O-disulpho-D-glucosamine structure at the reducing end of the chain. The molecular weight ranges between 3500 and 5500 daltons and the average molecular weight is about 4500 daltons. The degree of sulfation is about 2 per disaccharide unit.

Nadroparin calcium is prepared by nitrous acid degradation of heparin obtained from the intestinal mucosa of pigs. The majority of the components have a 2-O-sulpho-α-L-idopyranosuronic acid structure at the non-reducing end of the chain and a 6-O-sulpho-2,5-anhydro-D-mannitol structure at the reducing end of the chain. The average molecular weight is about 4500 daltons. The degree of sulfation is about 2.1 per disaccharide unit.

Parnaparin sodium is prepared by hydrogen peroxide and copper(II)acetate degradation of heparin obtained from the intestinal mucosa of pigs. The majority of the components have a 2-N,6-O-sulpho-2,5-D-glucosamine structure at the reducing end of the chain. The molecular weight ranges between 4000 and 5000 daltons. The degree of sulfation is about 2.15 per disaccharide unit.

Reviparin sodium is prepared by nitrous acid degradation of heparin obtained from the intestinal mucosa of pigs. The majority of the components have a 2-O-sulpho-α-L-idopyranosuronic acid structure at the non-reducing end of the chain and a 2-N,6-O-disulpho-D-mannitol structure at the reducing end of the chain. The molecular weight of 90% of the components is between 2000 and 8000 daltons and the average molecular weight is 3500 to 4500 daltons. The degree of sulfation is about 2.2 per disaccharide unit.

Tinzaparin sodium is prepared by enzymatic degradation of the intestinal mucosa of pigs. The majority of the components have a 2-O-sulpho-4-enopyranosuronic acid structure at the non-reducing end of the chain and a 2-N,6-O-disulpho-D-glucosamine structure at the reducing end of the chain. The molecular weight of 70% of the components is between 1500 and 10,000 daltons and the average molecular weight is about 4500 daltons. The degree of sulfation is 2.0 to 2.5 per disaccharide unit.

SUMMARY OF THE INVENTION

This invention provides a drug delivery device comprising:

a matrix comprising a therapeutically effective amount of a heparinic anticoagulant, and means for maintaining the matrix in contact with a mucosal surface for a time sufficient to allow release of the heparin to the mucosa.

In a preferred embodiment of the invention the matrix further comprises a penetration enhancer. In another preferred embodiment the heparinic anticoagulant is a low molecular weight heparin.

The present invention also provides a method of achieving and/or maintaining a therapeutically effective blood level of a heparinic anticoagulant in a mammal comprising the steps of:

i) providing a device of the invention;

ii) placing the device in contact with a mucosal surface of the mammal; and iii) allowing the device to remain in contact with the mucosal surface for a time sufficient to establish and/or maintain a therapeutically effective blood level of the heparinic anticoagulant.

DETAILED DESCRIPTION OF THE INVENTION

Figure 1:
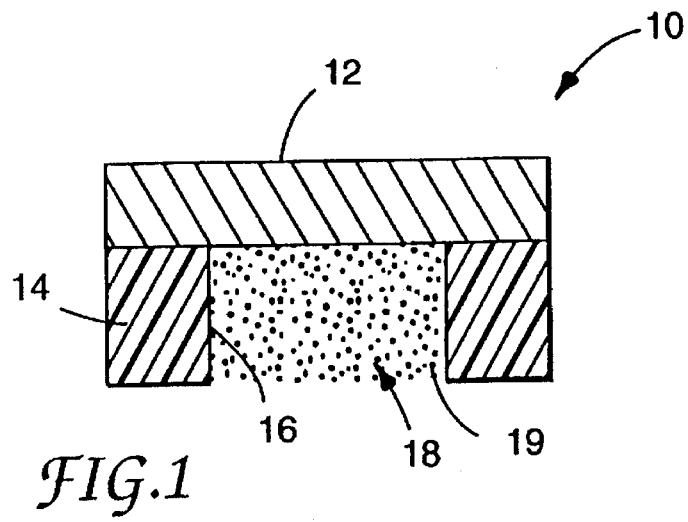
FIG. 1 is a cross sectional view of one embodiment of the invention.

This invention provides drug delivery devices comprising a matrix containing a heparinic anticoagulant. The matrix can be in any form suitable for containing the heparinic anticoagulant and releasing it to a mucosal surface such as, for example, a gel, a tablet, or a powder.

When the matrix is a gel it is preferably an aqueous gel comprising, in addition to the heparinic anticoagulant, a gel-forming agent. The gel-forming agent can be any pharmaceutically acceptable agent that is capable of forming a water based gel and does not have a detrimental effect on other components of the matrix. Examples of suitable gel-forming agents include gums (e.g., pectin); montmorillonite clays (e.g., Veegum); crosslinked polysaccharides (e.g., dextran crosslinked with epichlorohydrin) and polymeric acrylic resins (e.g., CARBOPOL™ resins, B. F. Goodrich, Specialty Polymers and Chemicals Division, Cleveland, Ohio) reacted with a base. Particularly preferred are the CARBOPOL™ resins, such as CARBOPOL™ 934P, CARBOPOL™ EX165, and CARBOPOL™ EX214.

When the matrix is in the form of a tablet it preferably contains, in addition to the heparinic anticoagulant, a pharmaceutically acceptable binder. Examples of suitable binders include cellulose derivatives such as carboxymethylcellulose, hydroxypropylcellulose, or hydroxypropylcellulose; starches such as rice starch; silicas such as AEROSIL™ 200 colloidal silicon dioxide (Degussa Corp, Teeterboro, N.J.) and polymeric acrylic resins such as the CARBOPOL™ resins described above.

When the matrix is in the form of a powder it can be a powdered heparinic anticoagulant alone or it can contain additional components such as penetration enhancers (discussed below). Most preferred is a lyophilized powder matrix, prepared by lyophilizing an aqueous gel that contains the heparinic anticoagulant. Such a lyophilized powder matrix, when used with the preferred mucoadhesive described in detail below, has been found to afford a device having superior adhesion and drug delivery characteristics.

A heparinic anticoagulant is present in a device of the invention in a therapeutically effective amount. The amount that constitutes a therapeutically effective amount varies according to the particular heparinic anticoagulant being used, the condition being treated, the surface area of the matrix, and on the other components present in the matrix containing the heparin. Accordingly it is not practical to enumerate particular preferred amounts but such can be readily determined by those skilled in the art with due consideration of these factors. Generally, however, in embodiments where the matrix is in the form of a gel, a heparinic anticoagulant is present in an amount of about two to about sixty percent, preferably about five to about twenty percent, by weight based on the total weight of the gel. In embodiments where the matrix is in the form of a tablet, a heparinic anticoagulant is present in an amount of about one to ninety-five percent, preferably about thirty to sixty-five percent, by weight based on the total weight of the tablet. In embodiments where the matrix is in the form of a powder, a heparinic anticoagulant is present in an amount of about one to ninety-five percent, preferably about thirty to sixty-five percent, by weight based on the total weight of the powder.

The heparinic anticoagulant used in a device of the invention can be any oligosaccharide having anticoagulant properties. Suitable heparinic anticoagulants include heparins or active fragments and fractions thereof from natural, synthetic, or biosynthetic sources. Also suitable are derivatives of any of the above (such as salts and esters). Exemplary heparinic anticoagulants include dalteparin sodium, enoxaparin sodium, nadroparin calcium, parnaparin sodium, reviparin sodium, and tinzaparin sodium.

Anti-Xa activity of heparins has been said to arise out of a pentasaccharide binding site having the structure

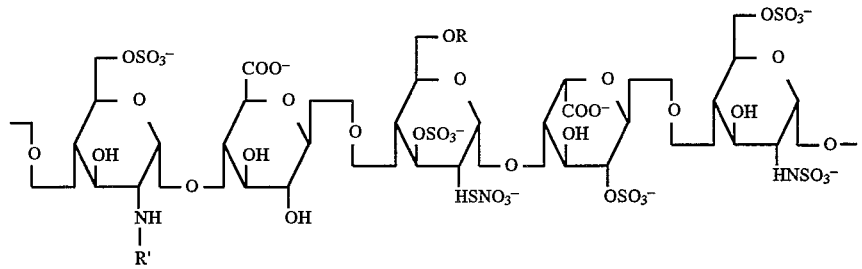

wherein R is H or —SO$_3^-$ and R' is —SO$_3^-$ or —COCH$_3$. Synthetic heparinic anticoagulants containing this pentasaccharide sequence are suitable and can be prepared, e.g., as described in Biochem. Biophys. Res. Commun. 1983, 116, 492 (Choay et al.) and references cited therein.

Other heparinic anticoagulants suitable for use in a device of the invention include oligosaccharide and mucopolysaccharide glycosaminoglycans such as those disclosed in U.S. Pat. No. 5,013,724 (Petitou et al.), low molecular weight heparins such as those disclosed in U.S. Pat. No. 4,990,502 (Lormeau et al.), xylan sulfates such as those disclosed in U.S. Pat. Nos. 4,713,373 and 4,699,900 (Bayol et al.), and low molecular weight heparins, heparin fragments, heparin fractions such as those disclosed in U.S. Pat. No. 5,110,918 (Casu et al.), oligosaccharide fractions disclosed in U.S. Pat. No. 5,084,564 (Vila et al.), and low molecular weight heparin derivatives disclosed in Patent Application WO92/11294 (Della Valle et al.). Low molecular weight heparins are preferred. Low molecular weight heparin Bioparin BF-611 (Bioiberica) is most preferred.

It has been found that incorporation of certain penetration enhancers significantly enhances penetration rate of heparinic anticoagulants in vivo measured using the rat model described below. Hence, the matrix can further comprise a penetration enhancer. Suitable penetration enhancers include anionic surfactants (e.g., sodium dodecyl sulfate); cationic surfactants (e.g., palmitoyl DL carnitine chloride); nonionic surfactants (e.g., laureth 9, polyoxyethylene 20 stearyl ether, polyoxyethylene 20 cetyl ether, polyoxyalkylenes); lipids (e.g., dodecanoyl L-α-phosphatidyl choline); bile salts (sodium deoxycholate, sodium taurodeoxycholate); and related compounds (e.g., sodium tauro-24,25-dihydrofusidate). The preferred penetration enhancers are nonionic surfactants, particularly laureth 9. The enhancers are dissolved or dispersed substantially uniformly in the matrix.

The matrix can contain other ingredients, for example excipients such as flavorings or dyes and the like in amounts readily determined by those skilled in the art.

The device of the invention comprises means for maintaining the matrix in contact with a mucosal surface. Suitable means include adhesives known to adhere to mucosa (referred to herein as "mucoadhesives"). A mucoadhesive for use in a device of the invention can be any composition that adheres to a mucosal surface. Suitable mucoadhesives include those disclosed in U.S. Pat. Nos. 4,615,697 (Robinson) and 5,113,860 (McQuinn) (incorporated herein by reference).

Preferred mucoadhesive compositions include those disclosed in Patent Application No. WO 90/06505 incorporated herein by reference. Such preferred mucoadhesives comprise:

1) a particulate polymeric resin with an average particle size of less than or equal to about 100 µm, preferably between about 1 µm and about 80 µm, more preferably between about 1 µm and about 30 µm, and most preferably between about 2 µm and about 10 µm, and comprising at least about 55% by weight of carboxylic acid moieties based on the total weight of the polymeric resin; and 2) from about 20 parts to about 250 parts by weight of a hydrophobic elastomeric component, preferably about 20 parts to about 150 parts, and most preferably 25 to about 75 parts by weight, based on 100 parts by weight of the resin;

wherein the resin is dispersed substantially throughout the elastomeric component, and which composition contains less than about 10%, preferably less than about 6%, more preferably less than about 4%, and most preferably less than about 2% by weight of water based on the total weight of the resin.

The polymeric resin component of the preferred mucoadhesive comprises at least about 55% by weight of carboxylic acid moieties based on the total weight of the resin. Suitable carboxylic acid-containing monomers include acrylic acid, maleic acid, itaconic acid, citraconic acid, methacrylic acid, and the like, and combinations thereof. Acrylic acid is preferred. The polymeric resin can also comprise minor amounts (e.g., less than about 20 percent by weight based on the total weight of all monomers in the polymer) of comonomers that are polymerizable with the carboxylic acid-containing monomer, such as methyl vinyl ether, lower alkyl (meth) acrylates, and the like.

Linear polyacrylic acid resins with a molecular weight between about 400,000 and about 5,000,000 have been found to be suitable for use in a composition of the invention. More preferred, however, are crosslinked resins. Most preferred resins include those comprising polyacrylic acid with a molecular weight between about 750,000 and about 4,000,000, preferably about 2,000,000 to about 4,000,000, and more preferably about 3,000,000, crosslinked with about 0.75% to about 2% by weight, based on the total weight of the resin, of a polyalkenyl polyether such as an allyl ether of sucrose or an allyl ether of pentaerythritol. Particularly preferred resins of this type include the resins available under the trade designation CARBOPOL™ resin (e.g., CARBOPOL™ resins EX165, EX214, 910, 934, 934P, 941, 951, and 1342 from B. F. Goodrich Co., Specialty Polymers and Chemical Division, Cleveland, Ohio). Another suitable resin is "polycarbophil", A. H. Robins Co., Richmond, Va., and described in USP XX as a polyacrylic acid crosslinked with divinylglycol.

The carboxylic acid moieties in the resin can be present as formal protonated carboxylic acid functional groups or as neutralized carboxylate salts. For example, a polyacrylic acid resin or a crosslinked resin such as those enumerated above can be partially neutralized by a base of an alkali metal, or by a base of a divalent or trivalent metal (e.g., $Zn^{+2}$, $Ca^{+2}$, $Mg^{+2}$, or $Al^{+3}$). Basic polyamines such as Eudragit E™ (a copolymer of dimethylaminoethyl methacrylate and neutral methacrylates, Rohm Pharma, Weiterstadt, Germany) are also suitable for use in neutralizing a resin. Preferred bases include NaOH.

Examples of materials suitable for use in an elastomeric component in these preferred mucoadhesives include: hydrocarbons such as block styrene-butadiene-styrene copolymers and block styrene-isoprene-styrene copolymers, such as those available from Shell Chemical Co. as Kraton™ rubbers, polyolefins such as polyisobutylenes such as VISTANEX™ LM-MH polyisobutylene (viscosity average molecular weight about 53,000), VISTANEX™ L-80 polyisobutylene (viscosity average molecular weight about 900,000), and VISTANEX™ L-100 polyisobutylene (viscosity average molecular weight about 1,200,000), all from Exxon Chemical, Houston Tex., polybutadienes, butyl rubber (a copolymer of isobutylene and isoprene), and isoprene rubbers, e.g., polyisoprene (such as that available as LIR-50 polyisoprene from Arakawa Chemical Co., Chicago, Ill. and NATSYN™ polyisoprene from Goodyear, Akron, Ohio); functionalized polyolefins such as functional polyisoprenes, e.g., carboxy-functional polyisoprenes (such as that available as LIR-410 polyisoprene, also from Arakawa) and hydroxy-functional polyisoprenes (such as that available as LIR-506 polyisoprene, Arakawa); and mixtures and blends of two or more of the foregoing. Hydrocarbons are the most preferred materials for use in an elastomeric component.

A device of the invention preferably comprises a backing. The backing can be any flexible film that prevents bulk fluid flow, provides a barrier to loss of heparinic anticoagulant and is substantially inert to the ingredients of the matrix. The backing material can be any of the conventional materials used as backings for tapes or dressings such as polyethylene, polypropylene, ethylene-vinyl acetate copolymer, polyurethane and the like. Also, a layer of hydrophobic elastomer can function as a backing. Preferred backing materials include an acrylate pressure sensitive adhesive coated polyurethane film such as TEGADERM™ surgical dressing (3M Company, St. Paul, Minn.).

DESCRIPTION OF THE PREFERRED EMBODIMENTS

FIG. 1 shows a device, generally designated by reference numeral 10. Device 10 represents an embodiment of the invention comprising (i) a backing layer, (ii) a matrix adjacent one surface of the backing layer and comprising a therapeutically effective amount of a heparinic anticoagulant, the matrix having a smaller periphery than the backing layer such that a portion of the backing layer extends outward from the periphery of the matrix, and (iii) a mucoadhesive layer that covers the outward extending portion of the backing layer. The underside of backing layer 12 carries a layer of mucoadhesive 14 around its periphery. The backing 12 and the peripheral ring of mucoadhesive 14 taken together form reservoir 16. Reservoir 16 contains a matrix 18 with a heparinic anticoagulant 19 dispersed through it.

Figure 2:
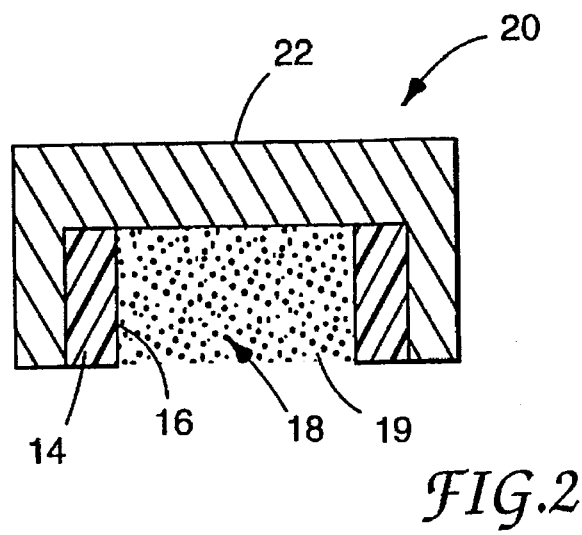
FIG. 2 is a cross sectional view of a second embodiment of the invention.

The device of FIG. 2, generally designated by reference numeral 20, is similar in design to the device of FIG. 1 except that backing 22 covers substantially all of device 20 other that the portion intended to be in direct contact with a mucosal surface.

It has been found that there is an optimal rate of hydration of the preferred mucoadhesive described above. Depending upon the particular type of matrix present in a device of the invention, mucoadhesive hydration via the walls of reservoir 16 in FIGS. 1 or 2 can occur at a faster than optimal rate, resulting in premature loss of adhesion.

Figure 3:
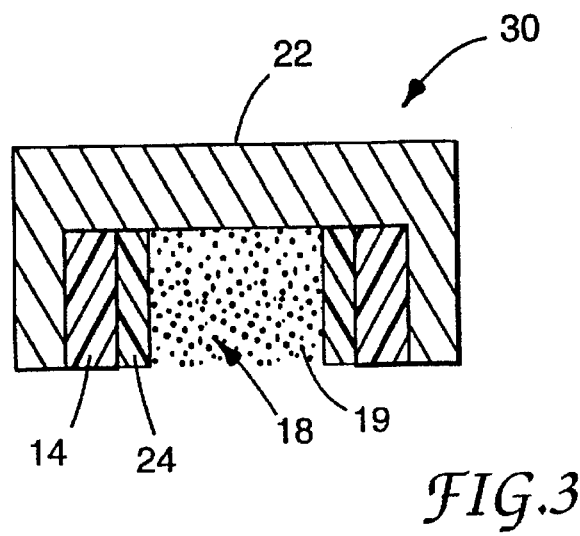
FIG. 3 is a cross sectional view of a third embodiment of the invention.

FIG. 3 shows device 30 similar in design to device 20 of FIG. 2. Device 30 comprises barrier element 24 between matrix 19 and mucoadhesive 14 and reservoir 16 containing matrix 18. Barrier element 24 serves to isolate the mucoadhesive from the matrix. It is preferably substantially impermeable to water and to the mucosal fluids that will be present at the intended site of adhesion. A device having such a barrier element can be hydrated only through a surface that is in contact with the mucosa, and it is not hydrated via the reservoir. This configuration therefore is particularly desirable in an embodiment employing an aqueous gel as the matrix.

A device of the invention can be prepared by general methods well known to those skilled in the art. The preferred mucoadhesives can be prepared according to the methods set forth in Patent Application No. WO 90/06505. Likewise a matrix can be readily prepared by those skilled in the art.

When the matrix is in the form of a gel, it is prepared by first combining water and the gel-forming agent to form a gel. Optional excipients such as penetration enhancers are added and mixed in to form a homogeneous gel followed by the addition of the heparinic anticoagulant with mixing to homogeneity to afford a gel formulation. When the matrix is in the form of a tablet, a bulk powder formulation is initially prepared by combining the binding agent with optional excipients such as a penetration enhancer to form a homogenous mixture, then the heparinic anticoagulant is added and mixed to homogeneity. The bulk powder is then compressed using conventional means to form tablets. When the matrix is in the form of a powder, a bulk powder formulation as prepared for the tablets can be used or, alternatively, a gel formulation can be lyophilized to provide a powder.

Devices of the invention such as those represented by FIGS. 1, 2, and 3 can be prepared by die cutting a sheet of mucoadhesive into individual patches such that a central portion of the patch is removed (e.g., a patch in the shape of a ring with an inner diameter of 1.3 cm and an outer diameter of 2.5 cm). A backing is then laminated to one surface of the mucoadhesive patch resulting in the formation of a reservoir. A matrix containing a heparinic anticoagulant is then placed into the reservoir portion. Alternatively, a device involving a lyophilized powder matrix can be prepared by first preparing an aqueous gel matrix, filling it into the reservoir, and lyophilizing the resulting device.

A device of the invention can be used to treat conditions capable of treatment with a heparinic anticoagulant (e.g., treatment and prophylaxis of venous thromb-embolism). Generally, a device of the invention is applied to a mucosal surface, such as the oral mucosa, e.g., the buccal mucosa or gingival mucosa, of a mammal and allowed to remain for a time sufficient to establish or maintain a therapeutically effective blood level of the heparinic anticoagulant in order to achieve the intended therapeutic effect. The time period during which the device is to remain in place depends on the particular device and on the intended therapeutic effect. Appropriate time periods can be readily selected by those skilled in the art.

Procedures and test methods used in connection with devices of the invention are set forth below.

IN VITRO PENETRATION TEST METHOD

Release of heparinic anticoagulant from a particular matrix is determined using a diffusion cell according to the following method.

A polyvinylpyrrolidone/cellulose acetate hydrogel is prepared in the following manner. A 9.6 g portion of polyvinylpyrrolidone (average molecular weight of 360,000; Aldrich Chemical Company) and a 2.4 g portion of cellulose acetate are dried at 100° C. under vacuum for 1 hour and then allowed to cool to ambient temperature in a desiccator. The dried materials are combined in a glass jar with acetone (108 mL) and methanol (12 mL). The jar is flushed with nitrogen, sealed and then placed on a mixer for at least 12 hours. A spin-caster cylinder is lined with a silicon release liner, placed in the spin-caster and then purged with nitrogen for 20 minutes. The nitrogen line is removed, a portion of the polyvinylpyrrolidone/cellulose acetate solution is injected into the cylinder, the nitrogen line is reattached and the spin caster is run for at least 12 hours. The resulting dry hydrogel is removed from the cylinder and stored in a jar. Prior to use the hydrogel is hydrated in demineralized water for at least 30 minutes.

A section of hydrated hydrogel is mounted onto the lower (receptor cell) portion of a diffusion cell (2 cm$^2$ unless otherwise indicated). The matrix to be tested is placed in the center of the section of hydrogel then the upper (donor cell) portion of the diffusion cell is clamped onto the lower portion. A portion of water is added to the receptor cell sufficient for the water to contact the hydrogel. The sampling port is covered with PARAFILM™ laboratory film. The diffusion cell is then placed on a heat magnetic stirrer at 37° C. All those cells and the magnetic stirrer are placed in a plexiglass box in order to maintain an environment of 37° C. around the cells. The medium in the receptor cell is stirred throughout the experiment by means of a magnetic stir bar. The entire volume of medium is removed from the receptor cell at specified time intervals and immediately replaced with fresh medium.

The withdrawn medium is analyzed for heparinic anticoagulant as follows. A sample is diluted as appropriate with demineralized water or with isotonic saline medium (0.2% NaCl in water). A 5 mL portion of the diluted sample is placed in a centrifuge tube. A 2.5 mL portion of toluidine blue solution (0.005% toluidine blue in 0.2% saline solution) is added to the tube which is then placed in a vortex mixer for 30 seconds. Hexanes (5 mL) is added to the tube which is then vortexed for 30 seconds. The tube is centrifuged at 3000 rpm for 5 minutes. The organic and aqueous phases are separated. The aqueous phase is put through a 0.45 μm filter and the absorbance of the filtrate at 625 nm is determined using a spectrophotometer. Results are reported as the cumulative percent of the heparinic anticoagulant originally present in the matrix that has penetrated the hydrogel and passed into the medium.

IN VIVO RAT MODEL

The in vivo delivery of heparinic anticoagulant from a gel is determined using a rat model.

This method uses rats of 220 to 500 grams in weight. Wistar rats are the preferred strain. The rats are anesthetized with ether and then a 2 cm vertical incision is made first through the skin and then through the underlying muscle. The esophagus is isolated and tied off with a surgical ligature. The incision is closed with a surgical stapler. After surgery the rats are dosed with the gel by syringe administration with half of the total dose in each cheek. The rats are slightly reanesthesized for dosing and blood withdrawal. Blood samples are withdrawn at 0, 1, 2, 3 and 4 hours post dose. Heparinic anticoagulant concentrations in plasma are determined by an enzymatic method measuring anti Xa using a test kit (Stachrom™ Heparin from Diagnostica Stago, 9 rue des Freres Chausson, 92600 Asnieres-sur Seine, France). Results are reported as the number of anti Xa units per mL of plasma.

IN VIVO DOG MODEL

The in vivo delivery of heparinic anticoagulant from a device of the invention is determined using a dog model.

This method uses male and female Beagle dogs, from 14 to 20 kg. Two devices of the invention are placed on either the cheek buccal area or on the gum. Blood samples are withdrawn at specified times and plasma levels of heparinic anticoagulant are determined as described above in connection with the rat model.

PREPARATION OF MUCOADHESIVE

Solvent Casting

A mucoadhesive containing 50 percent by weight CARBOPOL™ 934P resin (B. F. Goodrich), 20 percent by weight of VISTANEX™ L100 polyisobutylene and 30 percent by weight of VISTANEX™ LMMH polyisobutylene (Exxon Chemical Company) was prepared as follows.

A sample of CARBOPOL 934P resin (100 g) was placed in 200 g of a 1:1 (v/v) mixture of toluene and hexane. The solution was stirred for 5 minutes. A stock solution containing VISTANEX LM-MH (60 g) and VISTANEX L-100 (40 g) in a 1:1 (v/v) mixture of toluene and hexane (192.3 g) was prepared and added. The combined mixture was stirred for 1 hour at room temperature.

A sheet material was prepared by knife coating the above prepared solution onto a siliconized release liner at a wet thickness of about 3 mm and drying for 3 hours at 30° C. Patches of the desired shape and size were die-cut from the sheet and a backing applied as desired.
Milling A composition was prepared using a two-roll mill as follows:

A polyisobutylene (43.75 g of VISTANEX LM-MH) was added to a Farrell-Birminghan two-roll mill and milled until it was distributed on the rollers. A polyisoprene (6.25 g NATSYN 2210, Goodyear) was added and milling was continued until a substantially homogeneous mixture was obtained. CARBOPOL 934P (50 g) was added slowly with milling and milling was continued until a uniform composition was obtained. It was necessary to periodically remove the material from the rollers, form it into a ball, and remill. The composition was removed from the mill by scraping the rollers.

A sample of the composition was pressed between two sheets of siliconized coated release liner in a platen press heated to about 40° C. to afford a laminate having a thickness of about 1 mm. Patches of the desired shape and size were die-cut from the sheet and a backing applied as desired.

PREPARATION OF THE SODIUM SALT OF CARBOPOL RESIN

CARBOPOL resin (40 g) is added with vigorous stirring to a solution containing sodium hydroxide (16 g) in methanol (340 mL). The resulting mixture is stirred for 7 hours then allowed to stand at ambient conditions for about 48 hours. The mixture is stirred again then the salt is dried in an oven at 65° C. for 3 to 4 hours. The dried salt is stored in a bottle under

TABLET PREPARATION

TABLET 1

A bulk powder was prepared by blending the sodium salt of CARBOPOL 934P resin (0.023 g) with sodium chloride (0.023 g) in a mortar. Sodium dodecyl sulfate (0.07 g, Sigma, St. Louis, Mo.) was then blended into the mixture followed by low molecular weight heparin (0.14 g, mean molecular weight 5200, Bioiberica, Barcelona, Spain). Individual portions of this bulk powder formulation were weighed out then compressed by hand to form tablets. The composition of the resulting tablet is shown in Table 1 below where all amounts are in mg.

TABLETS 2–6

Using the general method set forth above in connection with Tablet 1, a series of bulk powder formulations were prepared and compressed into tablets. The compositions are shown in Table 1 below where all amounts are in mg.

TABLET 7

A bulk powder formulation was prepared by slowly adding Laureth-9 (0.07 g, $C_{12}H_{25}(OCH_2CH_2)_nOH$ where n has an average value of 9, Sigma) to a mixture of the sodium salt of CARBOPOL 934P resin (0.023 g) and AEROSIL 200 (0.035 g, colloidal silicon dioxide, Degussa Corp, Teeterboro, N.J.) in a mortar and then blending to provide a homogeneous mixture. Sodium chloride (0.023 g) was blended into the mixture followed by the low molecular weight heparin (0.14 g, mean molecular weight 5200, Bioiberica, BarCelona, Spain). The resulting powder was compressed to form tablets. The composition of the individual tablets is shown in Table 1 below where all amounts are in mg.

Release from Tablets 1–7 was determined using the in vitro test method described above. The results are shown in Table 2 below where each value represents the average from 3 diffusion cells.

TABLE 1

| Ingredient | Tablet Number | | | | | | |
|---|---|---|---|---|---|---|---|
| | 1 | 2 | 3 | 4 | 5 | 6 | 7 |
| CARBOPOL 934P sodium salt | 2.3 | 1.15 | — | — | — | — | 1.15 |
| Carboxymethyl-cellulose[1] | — | — | — | 2.3 | — | — | — |
| Rice starch[2] | — | — | — | — | 2.3 | — | — |
| CARBOPOL 910 sodium salt | — | — | — | — | — | 2.3 | — |
| Sodium dodecyl sulfate | 7 | 7 | 7 | 7 | 7 | 7 | — |
| Laureth-9 | — | — | — | — | — | — | 7 |
| AEROSIL 200 | — | — | — | — | — | — | 3.5 |
| Sodium chloride | 2.3 | 2.3 | 2.3 | 2.3 | 2.3 | 2.3 | 2.3 |

TABLE 1-continued

| Ingredient | Tablet Number | | | | | | |
|---|---|---|---|---|---|---|---|
| | 1 | 2 | 3 | 4 | 5 | 6 | 7 |
| Low molecular weight heparin | 14 | 14 | 14 | 14 | 14 | 14 | 14 |

[1] Carboxymethylcellulose 7H4XF from Hercules
[2] Rice starch from Lambert & Riviere

TABLE 2

Cumulative Percent Heparin Released

| Tablet | Time (hours) | | | |
|---|---|---|---|---|
| | 1 | 3 | 5 | 24 |
| 1 | 10 ± 0.06 | 20.4 ± 0.06 | 28.2 ± 0.31 | 41.5 ± 0.21 |
| 2 | 14 ± 1.47 | 23.5 ± 1.04 | 34.0 ± 0.87 | 45.1 ± 0.95 |
| 3 | 14.3 ± 1.15 | 25.3 ± 1.85 | 36.2 ± 2.99 | 52.0 ± 3.64 |
| 4 | 14.8 ± 0.4 | 19.3 ± 1.3 | 27.4 ± 1.1 | 34.1 ± 1.62 |
| 5 | 14.6 ± 0.45 | 28.2 ± 1.14 | 28.2 ± 1.14 | 44.8 ± 1.08 |
| 6 | 11.8 ± 1.82 | 20.7 ± 1.59 | 29.7 ± 0.35 | 44.3 ± 0.35 |
| 7 | 43.7 ± 2.01 | 59.8 ± 2.01 | 76.2 ± 1.88 | 90.1 ± 1.76 |

TABLETS 8–13

Using the general method set forth above in connection with Tablet 1, except that the sodium chloride was omitted, a series of bulk powder formulations was prepared then compressed into tablets having an area of 0.5 cm$^2$. The composition of the individual tablets is shown in Table 3 below where all amounts are in mg. Release from these tablets was determined using the in vitro test method described above. The results are shown in Table 4 below where each value is the average of 3 diffusion cells.

TABLE 3

| Ingredient | Tablet Number | | | | | |
|---|---|---|---|---|---|---|
| | 8 | 9 | 10 | 11 | 12 | 13 |
| CARBOPOL 934P sodium salt | — | — | 2.3 | — | — | 2.3 |
| Hydroxypropylmethyl-cellulose[1] | 2.3 | — | — | 2.3 | — | — |
| Hydroxypropylcellulose[2] | — | 2.3 | — | — | 2.3 | — |
| Sodium dodecyl sulfate | 7 | 7 | 7 | — | — | — |
| Sodium taurodihydro-fusidate[3] | — | — | — | 7 | 7 | 7 |
| Low molecular weight heparin[4] | 14 | 14 | 14 | 14 | 14 | 14 |

[1] METOLOSE ™ 90SH 15000, Seppic
[2] LHPC-LH-21, Seppic
[3] Leo
[4] BF611, mean molecular weight 3950 to 4400, Bioiberica, Barcelona, Spain

TABLE 4

Cumulative Percent Heparin Released

| Tablet | Time (hours) | | | |
|---|---|---|---|---|
| | 1 | 3 | 5 | 24 |
| 8 | 19.3 ± 0.61 | 25.9 ± 1.48 | 29.8 ± 2.97 | 45.3 ± 7.13 |
| 9 | 16.6 ± 1.63 | 28.3 ± 6.08 | 37.0 ± 5.8 | 50.0 ± 12.6 |
| 10 | 6.3 ± 3.43 | 17.3 ± 5.14 | 25.2 ± 9.05 | 42.0 ± 5.95 |

TABLE 4-continued

Cumulative Percent Heparin Released

| Tablet | Time (hours) | | | |
|---|---|---|---|---|
| | 1 | 3 | 5 | 24 |
| 11 | 61.6 ± 4.01 | 86.6 ± 3.09 | 100 ± 2.46 | 104.2 |
| 12 | 36.0 ± 8.06 | 50.3 ± 10.47 | 59.3 ± 13.15 | 73.5 ± 12.09 |
| 13 | 40.4 ± 7.18 | 77.3 ± 6.06 | 87.0 ± 8.79 | 96.2 ± 2.85 |

TABLETS 14–20

Using the general methods described above, a series of tablets (0.25 cm$^2$) was prepared in which a variety of pluronic acids (BASF) served as the penetration enhancers. The composition of the individual tablets is shown in Table 5 below where all amounts are in mg. Release from these tablets was determined using the in vitro test method described above. The results are shown in Table 6 below where each value is the average of 3 diffusion cells.

TABLE 5

| Ingredient | Tablet Number | | | | | | |
|---|---|---|---|---|---|---|---|
| | 14 | 15 | 16 | 17 | 18 | 19 | 20 |
| CARBOPOL 934P sodium salt | 2.3 | 2.3 | 2.3 | 2.3 | 2.3 | 2.3 | 2.3 |
| Pluronic acid F77 | 7 | — | — | — | — | — | — |
| Pluronic acid F87 | — | 7 | — | — | — | — | — |
| Pluronic acid F68 | — | — | 7 | — | — | — | — |
| Pluronic acid F88 prill | — | — | — | 7 | — | — | — |
| Pluronic acid F127 NF | — | — | — | — | 7 | — | — |
| Pluronic acid F108 prill | — | — | — | — | — | 7 | — |
| Pluronic acid F108 NF | — | — | — | — | — | — | 7 |
| Low molecular weight heparin[1] | 14 | 14 | 14 | 14 | 14 | 14 | 14 |

[1] BF611

TABLE 6

Cumulative Percent Heparin Released

| Tablet | Time (hours) | | | |
|---|---|---|---|---|
| | 1 | 3 | 5 | 24 |
| 14 | 51.6 ± 7 | 58.4 ± 5.47 | 59 ± 4.35 | 59.1 ± 4.47 |
| 15 | 60.6 ± 4.48 | 92.3 ± 0.97 | 92.3 ± 0.97 | 92.3 ± 0.97 |
| 16 | 66.4 ± 6.82 | 94.5 ± 4.23 | 101.4 ± 2.82 | 101.7 ± 2.78 |
| 17 | 76.6 ± 3.18 | 91.7 ± 3.78 | 96.5 ± 3.90 | 101.4 ± 5.65 |
| 18 | 59.0 ± 5.2 | 81 ± 6.65 | 82.2 ± 5.71 | 82.8 ± 5.21 |
| 19 | 63.9 ± 1.41 | 84.5 ± 4.6 | 92.7 ± 2.92 | 98.2 ± 3.13 |
| 20 | 71.5 ± 3.30 | 93.5 ± 2.19 | 93.5 ± 2.19 | 93.6 ± 2.39 |

GEL FORMULATIONS

Gel Formulation 1

Sodium hydroxide (96 mL of 1N) was added to a dispersion of CARBOPOL 934P resin (8 g) in demineralized water (qs 200 mL); the system thickened almost immediately to provide a clear stiff gel. Sodium dodecyl sulfate was added to the gel and mixed to homogeneity. Low molecular weight heparin (mean molecular weight from 3450 to 4004, Bioiberica, Barcelona, Spain) was added. Release was determined using the in vitro test method described above by spreading 150 mg portions of the formulation (each portion contained 128 mg gel, 7 mg sodium dodecyl sulfate and 15 mg of heparin) onto the hydrogel mounted in the diffusion cell. The results are shown in Table 7 below where each value is the average of 3 diffusion cells.

Gel Formulation 2

A gel formulation was prepared and tested according to the method above except that the sodium dodecyl sulfate was replaced with Laureth-9.

TABLE 7

| | Cumulative Percent Heparin Release | |
|---|---|---|
| Time (hours) | Gel Formulation 1 | Gel Formulation 2 |
| 1 | 17.9 ± 0 | 23.4 ± 0.99 |
| 3 | 43.75 ± 1.48 | 51.5 ± 1.94 |
| 5 | 61.9 ± 1.84 | 66.3 ± 0.85 |
| 24 | 85.4 ± 1.84 | 83.8 ± 1.67 |

Gel Formulations 3–5

A series of dextran gel formulations was prepared by slowly adding water to a mixture containing the several ingredients listed in Table 8 below. The compositions are shown in Table 8 below where all amounts are in mg. Release was determined as described in connection with Gel Formulation 1 and is shown in Table 9 below where each value is the average of 3 diffusion cells.

TABLE 8

| | Gel Formulation | | |
|---|---|---|---|
| Ingredient | 3 | 4 | 5 |
| SEPHADEX ™ G50-150[1] | 12.8 | — | — |
| SEPHADEX G25-300[1] | — | 12.8 | — |
| PDX ™ 6F 50-150[1] | — | — | 15.36 |
| Water | 115.2 | 115.2 | 112.64 |
| Laureth-9 | 7 | 7 | 7 |
| Low molecular weight heparin | 15 | 15 | 15 |

[1]Sigma

TABLE 9

| | Cumulative Percent Heparin Release | | |
|---|---|---|---|
| Time (hours) | Gel 3 | Gel 4 | Gel 5 |
| 1 | 20.4 ± 0.14 | 61.0 ± 8.13 | 38.2 ± 22.4 |
| 3 | 32.5 ± 2.26 | 63.8 ± 4.17 | 79.8 ± 5.3 |
| 5 | 32.5 ± 2.26 | 63.8 ± 4.17 | 83.4 ± 0.14 |
| 24 | 32.5 ± 2.26 | 63.8 ± 4.17 | 88.6 ± 2.19 |

Gel Formulation 6

A gel was prepared according to the method set forth above in connection with Gel Formulation 1. Standard heparin (molecular weight 10,000–15,000 with anti Xa of 185 units/mg, AKZO) was added at a concentration range of 0 to 100 mg of heparin per mL of gel. In vivo delivery was determined using the rat model described above. Each rat was dosed with 0.2 mL of gel formulation to provide the dose of heparin indicated in Table 10. The results are shown in Table 10 below.

TABLE 10

| | Mean anti Xa activity (anti Xa units/mL) | | | | |
|---|---|---|---|---|---|
| | Heparin dose (mg/rat) | | | | |
| Time (hours) | 1 | 3 | 5 | 10 | 20 |
| 0 | −0.03 | −0.03 | 0.00 | 0.02 | −0.03 |
| 1 | −0.03 | 0.07 | 0.17 | 0.24 | 0.39 |
| 2 | −0.07 | 0.02 | 0.23 | 0.33 | 0.41 |
| 3 | −0.09 | −0.02 | 0.15 | 0.26 | 0.40 |
| 4 | −0.03 | −0.01 | 0.13 | 0.21 | 0.36 |
| Number of rats | 3 | 3 | 8 | 29 | 8 |

Gel Formulation 7

A gel was prepared according to the method set forth above in connection with Gel Formulation 1. Low molecular weight heparin (molecular weight 3132, mean molecular weight 3450 daltons with anti Xa of 138 units/mg, Bioiberica, Barcelona, Spain) was added to the gel at a concentration range of 0 to 100 mg of heparin per mL of gel. In vivo delivery was determined using the rat model described above. Each rat was dosed with 0.2 mL of gel to provide the dose indicated in Table 11. The results are shown in Table 11 below.

TABLE 11

| | Mean Anti Xa Activity (anti Xa units/mL) | |
|---|---|---|
| | Dose (mg heparin/rat) | |
| Time (hours) | 2 | 5 |
| 0 | 0.02 | 0.02 |
| 1 | 0.10 | 0.61 |
| 2 | 0.16 | 1.25 |
| 3 | 0.16 | 1.24 |
| 4 | −0.07 | 0.94 |
| Number of rats | 2 | 6 |

Gel Formulation 8

A gel was prepared according to the method set forth above in connection with Gel Formulation 2. Laureth-9 was incorporated at 0, 2, 5 and 10 percent by weight based on the total weight of the gel formulation. Low molecular weight heparin (molecular weight 3132, mean molecular weight 3450 daltons with anti Xa of 138 units/mg, Bioiberica, Barcelona, Spain) was incorporated at a concentration of 10 mg of heparin per mL of gel. In vivo delivery was determined using the rat model described above. Each rat was dosed with hepari per rat. The results are shown in Table 12 below.

TABLE 12

| | Mean Anti Xa Activity (anti Xa units/mL) | | | |
|---|---|---|---|---|
| | Laureth-9 concentration (weight percent) | | | |
| Time (hours) | 0 | 2 | 5 | 10 |
| 0 | 0.02 | −0.05 | −0.06 | 0.01 |
| 1 | 0.10 | 0.63 | 1.44 | 1.68 |

TABLE 12-continued

| | Mean Anti Xa Activity (anti Xa units/mL) | | | |
|---|---|---|---|---|
| | Laureth-9 concentration (weight percent) | | | |
| Time (hours) | 0 | 2 | 5 | 10 |
| 2 | 0.16 | 0.99 | 1.84 | 1.54 |
| 3 | 0.16 | 0.60 | 1.50 | 0.96 |
| 4 | −0.07 | 0.51 | 0.80 | 0.52 |
| Number of rats | 2 | 4 | 11 | 4 |

Gel Formulation 9

A gel was prepared according to the method set forth above in connection with Gel Formulation 1. Laureth-9 was incorporated into the gel at 0 and 5 percent by weight based on the total weight of the gel formulation. Low molecular weight heparin (molecular weight 3132, mean molecular weight 3450 daltons) with anti Xa of 138 units/mg, Bioiberica, Barcelona, Spain) was incorporated at a concentration of 25 mg of heparin per mL of gel. In vivo delivery was determined using the rat model described above. Each rat was dosed with 0.2 mL of gel formulation to provide a dose of 5 mg of heparin per rat. The results are shown in Table 13 below.

TABLE 13

| | Mean Anti Xa Activity (anti Xa units/mL) | |
|---|---|---|
| | Laureth-9 Concentration (weight percent) | |
| Time (hours) | 0 | 5 |
| 0 | 0.02 | 0.00 |
| 1 | 0.61 | 4.27 |
| 2 | 1.25 | 3.99 |
| 3 | 1.24 | 4.34 |
| 4 | 0.94 | 2.80 |
| Number of rats | 6 | 6 |

Gel Formulation 10

A formulation was prepared according to the method set forth above in connection with Gel Formulation 1 except that the sodium dodecyl sulfate was eliminated and Brij 58 (polyoxyethylene 20 stearyl ether, Sigma) or Brij 78 (polyoxyethylene 20 cetyl ether, Sigma) was incorporated at 0 and 5 percent by weight based on the total weight of the gel formulation. Low molecular weight heparin (mean molecular weight 3949 daltons with anti Xa of 113 units/mg, Bioiberica, Barcelona, Spain) was incorporated at a concentration of 25 mg of heparin per mL of gel. In vivo delivery was determined using the rat model described above. Each rat was dosed with 0.2 mL of gel formulation to provide a dose of 5 mg of heparin per rat. The results are shown in Table 14 below.

TABLE 14

| | Mean Anti Xa Activity (anti Xa units/mL) | | |
|---|---|---|---|
| Time (hours) | Brij 58 | Brij 78 | no enhancer |
| 0 | −0.31 | −0.7 | −0.3 |
| 1 | 1.8 | 1.9 | 0.04 |
| 2 | 3.4 | 3.0 | 0.09 |
| 3 | 4.7 | 2.6 | 0.04 |
| 4 | 4.7 | 1.9 | 0.18 |
| 5 | 3.3 | 1.4 | −0.08 |
| 6 | 2.1 | 1.0 | −0.33 |
| Number of rats | 2 | 2 | 3 |

Gel Formulation 11

A formulation was prepared according to the method set forth above in connection with Gel Formulation 1, except that the sodium dodecyl sulfate was eliminated and the penetration enhancers shown in Table 15 below were incorporated at 2, 5 and/or 10 percent by weight based on the total weight of the gel formulation. Low molecular weight heparin (mean molecular weight from 3450 to 4950 daltons with anti Xa of 65 to 144 units/mg, Bioiberica, Barcelona, Spain) was incorporated at concentrations of 10, 25 and 50 mg of heparin per mL of gel. In vivo delivery was determined using the rat model described above. Each rat was dosed with 0.2 mL of gel formulation to provide the dose of heparin shown in Table 15, wherein "n" designates the number of rats studied. The values obtained were used to calculate the promoting effect (P for each formulation. The promoting effect was calculated using the equation given below:

$$P\% = \frac{Cmax(H+E) - Cmax(H)}{Cmax(H)} \times 100$$

where:

Cmax (H) is equal to the maximal anti Xa activity in plasma after heparin administration without enhancer and Cmax (H+E) is equal to the maximal anti Xa activity in plasma after heparin administration with the enhancer. The results are shown in Table 15 below.

TABLE 15

| Enhancer (wt percent) | Heparin dose (mg/rat) | P % | n |
|---|---|---|---|
| Laurocapram[1] + propylene glycol (2%) | 5 | −78 | 4 |
| Isopropyl myristate (5%) | 5 | −58 | 2 |
| Sodium glycocholate[2] (5%) | 5 | −50 | 2 |
| Laurocapram (5%) | 5 | −39 | 2 |
| Pyrrolidone (5%) | 5 | −31 | 2 |
| CHAPS[3] (5%) | 5 | +2 | 5 |
| Sodium deoxycholate[2] (2%) | 5 | +117 | 4 |
| Sodium deoxycholate (5%) | 5 | +122 | 5 |
| Sodium dodecyl sulfate (5%) | 5 | +189 | 5 |
| Laureth-9 (5%) | 5 | +300 | 7 |
| Laureth-9 (2%) | 2 | +455 | 4 |
| Laureth-9 (5%) | 2 | +955 | 4 |
| Laureth-9 (10%) | 2 | +825 | 4 |
| Sodium taurodeoxycholate[2] (5%) | 5 | +47 | 4 |
| Sodium taurodihydrofusidate[2] (10%) | 10 | +450 | 3 |
| Palmitoyl DL carnitine chloride (10%) | 10 | +142 | 3 |

TABLE 15-continued

| Enhancer (wt percent) | Heparin dose (mg/rat) | P % | n |
|---|---|---|---|
| L-α-Phosphatidylcholine, dodecanoyl[2] | 10 | +102 | 3 |

[1]AZONE ™, Nelson Research and Development, Irvine, CA
[2]Sigma
[3]3-[(3-Chloramidopropyl)dimethylammonio]-1-propanesulfonate, Sigma

EXAMPLE 1

A sheet of mucoadhesive (50% CARBOPOL 934P, 20% VISTANEX L100; 30% VISTANEX LMMH; prepared according to the solvent casting method described above) was die cut into rings having an outer diameter of 2.52 cm, an inner diameter of 1.38 cm and a thickness of 1 to 1.4 mm. A layer of TEGADERM™ surgical dressing was laminated to one side of the ring such that both the open area and the mucoadhesive were overlaid with the backing.

A gel was prepared according to the method set forth above in connection with Gel Formulation 1. Laureth-9 was incorporated at 2, 5 and 10 percent by weight based on the total weight of the formulation. Low molecular weight heparin (mean molecular weight 3450 daltons with anti Xa of 138 units/mg, Bioiberica, Barcelona, Spain) was incorporated at a concentration of 100 mg of heparin per mL of gel. The formulations were placed into the reservoir portions of the devices.

The in vivo delivery of low molecular weight heparin from these devices was then determined using the dog model described above. The devices were attached to the cheek areas. Two devices, each containing the same gel formulation, were used in each dog. The results are shown in Table 16 below.

TABLE 16

Mean Anti Xa Activity (anti Xa units/mL)

| Time (hours) | Laureth-9 Concentration (weight percent) | | |
|---|---|---|---|
| | 2 | 5 | 10 |
| 0 | −0.07 | −0.06 ± 0.01 | 0.04 ± 0.10 |
| 1 | 0.03 | −0.05 ± 0.08 | 0.12 ± 0.02 |
| 2 | 0.02 | 0.23 ± 0.11 | 0.35 ± 0.08 |
| 3 | 0.07 | 0.29 ± 0.04 | 0.42 ± 0.18 |
| 4 | 0.14 | — | 0.36 ± 0.26 |
| 5 | 0.13 | — | 0.27 ± 0.27 |
| 6 | 0.11 | — | — |
| Number of dogs | 1 | 2 | 3 |
| Dosage: mg heparin per dog | 30 | 31 ± 1.5 | 41 ± 1 |

EXAMPLES 2-4

A sheet of mucoadhesive (50% CARBOPOL 934P, 30 VISTANEX L100; 30% VISTANEX LMMH; prepared according to the solvent casting method described above) was die cut into rings having an outer diameter of 2.52 cm, an inner diameter of 1.38 cm and a thickness of 1 to 1.4 mm. A layer of TEGADERM™ surgical dressing was laminated to one side of the mucoadhesive ring such that only the mucoadhesive was overlaid with backing and the open area in the center was not overlaid. A layer of MICROPORE™ surgical tape (3M Company) was laminated to the same side of the ring such that both the open area and the mucoadhesive/backing laminate portion were overlaid.

Using the general method set forth above in connection with Tablet 1, a series of bulk powder formulations containing low molecular weight heparin (mean molecular weight 5300 daltons with anti Xa of 144 units/mg, Bioiberica, Barcelona, Spain) was prepared then compressed by hand to form tablets. The composition of the individual tablets is shown in Table 17 below where all amounts are in mg. Each tablet was placed into the reservoir portion of a device.

In vivo delivery of low molecular weight heparin from these devices was then determined using the dog model described above. Two devices, each containing the same tablet formulation, were used in each dog. The results are shown in Table 18 below where the values are the average from 4 dogs (Examples 3 and 4) or six dogs (Example 2).

TABLE 17

| | Example Number | | |
|---|---|---|---|
| Ingredient | 2 | 3 | 4 |
| CARBOPOL 934P sodium salt | 3.7 | 3.7 | 3.7 |
| Heparin LMW | 22.4 | 22.4 | 22.4 |
| Sodium dodecyl sulfate | 14.9 | 11.2 | 11.2 |
| Sodium chloride | 0 | 0 | 3.7 |
| Sorbitol | 0 | 3.7 | 0 |

TABLE 18

Mean Anti Xa Activity (anti Xa units/mL)

| Time (hours) | Example 2 | Example 3 | Example 4 |
|---|---|---|---|
| 0 | 0.05 ± 0.06 | 0.09 ± 0.06 | 0.03 ± 0.02 |
| 1 | 0.06 ± 0.07 | 0.09 ± 0.03 | 0.19 ± 0.05 |
| 2 | 0.11 ± 0.04 | 0.17 ± 0.07 | 0.23 ± 0.09 |
| 3 | 0.15 ± 0.06 | 0.17 ± 0.06 | 0.24 ± 0.11 |
| 4 | 0.13 ± 0.04 | 0.20 ± 0.07 | 0.24 ± 0.07 |
| 5 | 0.13 ± 0.07 | 0.11 | 0.23 ± 0.10 |
| 6 | 0.19 ± 0.09 | 0.07 ± 0.05 | 0.19 ± 0.07 |
| 7 | — | — | 0.15 ± 0.06 |

EXAMPLE 5

A sheet of mucoadhesive (50% CARBOPOL 934P, 20 VISTANEX L100; 30% VISTANEX LMMH; prepared according to the solvent casting method described above) was die cut into rings having an outer diameter of 2.52 cm, an inner diameter of 1.38 cm and a thickness of 1 to 1.4 mm. A layer of TEGADERM™ surgical dressing was laminated to one side of the mucoadhesive ring such that the open area in the center was overlaid. A layer of MICROPORE™ surgical tape was laminated to the same side of the ring such that both the mucoadhesive and the reservoir portion were overlaid. A tablet having the same formulation as that of Example 4 was placed in the reservoir of the device.

In vivo delivery of low molecular weight heparin from these devices was compared with that from the devices of Example 4 using the dog model described above with cross over administration in a single dog. The results are shown in Table 19 below.

TABLE 19

| | Anti Xa Activity (anti Xa units/mL) | |
|---|---|---|
| Time (hours) | Example 4 | Example 5 |
| 0 | 0.05 | −0.03 |
| 1 | 0.22 | 0.04 |
| 2 | 0.18 | 0.47 |
| 3 | 0.13 | 0.51 |
| 4 | 0.16 | 0.43 |
| 5 | 0.15 | 0.37 |
| 6 | 0.15 | 0.29 |
| 7 | — | 0.26 |

EXAMPLE 6

A sheet of mucoadhesive (50% CARBOPOL 934P, 6.25% NATSYN 2210, and 43.75% VISTANEX LMMH; prepared according to the two-roll milling method described above) was die cut into rings having an outer diameter of 2.52 cm, an inner diameter of 1.38 cm and a thickness of 1 to 1.4 mm. A layer of TEGADERM™ surgical dressing was laminated to one side of the mucoadhesive ring such that the open area in the center was overlaid. A layer of MICROPORE™ surgical tape was then laminated to the same side of the ring such that both the mucoadhesive and the reservoir portion were overlaid.

A gel was prepared according to the method set forth above in connection with Gel Formulation 1. Laureth-9 and low molecular weight heparin (molecular weight 3949 with anti Xa of 113 units/mg, Bioiberica, Barcelona, Spain) were then incorporated. The formulation was frozen at −20° C. then lyophilized using a LYOVAC GT2 (Leybold-Heraeus GMBH). The lyophilized material was ground to provide a powder that contained 15.3 percent by weight of CARBOPOL 934 P sodium salt (3.64 mg/unit), 28.2 percent by weight of Laureth-9 (7.0 mg/unit) and 56.4 percent by weight of low molecular weight heparin (14.0 mg/unit). The powder was loaded into the reservoir portion to afford a device substantially as illustrated in FIG. 3.

In vivo delivery from these devices was then determined using the dog model described above. Two devices were placed on each dog. The results are shown in Table 20 below.

TABLE 20

| | Anti Xa Activity (anti Xa units/mL) | | | | | |
|---|---|---|---|---|---|---|
| Time hours | Dog 1 | Dog 2 | Dog 3 | Dog 4 | Dog 5 | Dog 6 |
| 0 | 0.05 | −0.02 | −0.03 | 0.01 | −0.01 | −0.14 |
| 1 | 0.15 | 0.06 | 0.14 | 0.03 | 0.11 | −0.05 |
| 2 | 0.41 | 0.33 | 0.48 | 0.00 | 0.09 | 0.03 |
| 3 | 0.64 | 0.52 | 0.74 | 0.05 | 0.14 | 0.18 |
| 4 | 0.63 | 0.61 | 0.90 | 0.17 | 0.26 | 0.23 |
| 5 | 0.77 | 0.71 | 0.91 | 0.32 | 0.36 | 0.28 |
| 6 | 0.85 | 0.70 | 0.91 | 0.37 | 0.29 | 0.34 |
| 7 | 0.79 | 0.73 | 0.81 | 0.42 | 0.14 | 0.34 |
| 8 | 0.70 | 0.54 | 0.80 | — | — | 0.37 |
| Heparin dose mg/Kg | 1.94 | 1.84 | 1.87 | 1.68 | 1.44 | 1.58 |

Example 7

A sheet of mucoadhesive (30% CARBOPOL 934P, 61.25% VISTANEX LMMH, 8.75% NATSYN 2210, prepared according to the milling process described above) was die cut into rings having an outside diameter of 2.52 cm and an inside diameter of 1.38 cm. A backing player was applied as described in Example 6. A rubber ring having a wall thickness of 0.026 cm was then placed inside the mucoadhesive ring.

A gel formulation according to Gel Formulation 2 was prepared and filled into the cavity of the device. The filled device (substantially as illustrated in FIG. 3) was frozen at −53° C. and lyophilized in a LYOVAC GT2 apparatus. The lyophilized patch was tested according to the In Vitro Penetration Test Method set forth above using a 5 cm$^2$ diffusion cell. The results are shown in Table 21 below, where each number is the average of 3 independent determinations.

TABLE 21

| Cumulative Percent Heparin Release | |
|---|---|
| Time (hours) | Mean |
| 1 | 57.7 ± 2.5 |
| 3 | 88.0 ± 5.9 |
| 5 | 93.6 ± 8.3 |
| 24 | 99.7 ± 8.2 |

EXAMPLE 8

A bulk powder formulation was prepared by slowly adding laureth 9 to CARBOPOL 934P sodium salt (prepared as described above) in a mortar. Low molecular weight heparin was then added. The powder contained, per unit, 2.8 mg CARBOPOL 934P sodium salt, 7.0 mg laureth 9, and 14.0 mg low molecular weight heparin (BF-611, Bioiberica, Barcelona, Spain). A patch as described in Example 6 containing this powder was prepared.

A patch containing a lyophilized powder was prepared according to Example 6 above.

The two patches were tested according to the In Vitro Penetration Test Method set forth above. The results are shown in Table 22 below, where each number is the average of 3 independent determinations.

TABLE 22

| Cumulative Percent Heparin Release | | |
|---|---|---|
| Time (hours) | Powder | Lyophilized Powder |
| 1 | 56.7 ± 3.1 | 48.8 ± 2.0 |
| 3 | 69.8 ± 3.4 | 74.7 ± 1.5 |
| 5 | 70.1 ± 3.7 | 79.8 ± 1.9 |
| 24 | 72.8 ± 2.7 | 87.5 ± 1.9 |

The devices described above were also tested in the In Vivo Dog Model. Results are shown below.

TABLE 23

| | Anti Xa Activity (anti Xa units/mL) | | | |
|---|---|---|---|---|
| | Dog 1 | | Dog 2 | |
| Time hours | Powder | Lyophilized Powder | Powder | Lyophilized Powder |
| 0 | 0.02 | 0.04 | 0.13 | 0.02 |
| 1 | 0.02 | 0.18 | 0.19 | 0.23 |

TABLE 23-continued

| | Anti Xa Activity (anti Xa units/mL) | | | |
|---|---|---|---|---|
| | Dog 1 | | Dog 2 | |
| Time hours | Powder | Lyophilized Powder | Powder | Lyophilized Powder |
| 2 | 0.15 | 0.32 | 0.19 | 0.36 |
| 3 | 0.22 | 0.51 | 0.25 | 0.50 |
| 4 | 0.37 | 0.57 | 0.29 | 0.41 |
| 5 | 0.37 | 0.69 | 0.32 | 0.49 |
| 6 | 0.44 | 0.70 | 0.39 | 0.52 |
| 7 | 0.45 | 0.68 | 0.31 | 0.40 |
| 8 | 0.43 | 0.70 | 0.28 | 0.41 |

What is claimed is:

1. A drug delivery device comprising:
   a gel, powder, or tablet matrix comprising a therapeutically effective amount of a heparinic anticoagulant, and
   an outer mucoadhesive portion disposed peripherally to the matrix, thereby forming a reservoir within which the matrix is disposed,
   said mucoadhesive portion being sufficient to maintain the matrix in direct contact with a mucosal surface for a time sufficient to allow release of the heparinic anticoagulant to the mucosal surface.

2. A device according to claim 1 wherein the heparinic anticoagulant is a low molecular weight heparin.

3. A device according to claim 1 wherein the heparinic anticoagulant has an average molecular weight between about 1000 and about 7500 daltons.

4. A device according to claim 1 wherein the heparinic anticoagulant has an average molecular weight between about 3500 and about 5500 daltons.

5. A device according to claim 1 wherein the heparinic anticoagulant is selected from the group consisting of dalteparin sodium, enoxaparin sodium, nadroparin calcium, parnaparin sodium, reviparin sodium and tinzaparin sodium.

6. A device according to claim 1 wherein the heparinic anticoagulant is present in the matrix in an amount of about 1 to about 95 percent by weight based on the total weight of the matrix.

7. A device according to claim 1 wherein the matrix is in the form of a gel.

8. A device according to claim 1 wherein the matrix is in the form of a tablet.

9. A device according to claim 1 wherein the matrix is in the form of a powder.

10. A device according to claim 1 wherein the matrix is in the form of a lyophilized powder.

11. A device according to claim 1 wherein the matrix further comprises a penetration enhancer.

12. A device according to claim 11 wherein the penetration enhancer is selected from the group consisting of sodium dodecyl sulfate, laureth 9, sodium deoxycholate, sodium tauro-24,25-dihydrofusidate, palmitoyl DL carnitine chloride, dodecanoyl L-α-phosphatidyl choline, polyoxyethylene 20 stearyl ether and polyoxyethylene 20 cetyl ether.

13. A device according to claim 11 wherein the penetration enhancer is present in the matrix in an amount of about 2 percent to about 10 percent by weight based on the total weight of the matrix.

14. A device according to claim 1 wherein the mucoadhesive comprises:
   i) a particulate polymeric resin with an average particle size of less than or equal to about 100 μm and comprising at least about 55 percent by weight of carboxylic acid moieties based on the total weight of the polymeric resin; and
   ii) from about 20 parts to about 250 parts by weight of a hydrophobic elastomeric component, based on 100 parts by weight of the resin, wherein the resin is dispersed substantially throughout the elastomeric component and wherein the mucoadhesive contains less than about 10% by weight of water based on the total weight of the resin.

15. A device according to claim 1, comprising:
   i) a backing layer,
   ii) a matrix adjacent one surface of the backing layer and comprising a therapeutically effective amount of a heparinic anticoagulant, the matrix having a smaller periphery than the backing layer, wherein a portion of the backing layer extends outward from the periphery of the matrix, and
   iii) a mucoadhesive layer that covers at least part of the outward extending portion of the backing layer.

16. A device according to claim 1, comprising:
   i) a backing layer;
   ii) a matrix adjacent one surface of the backing layer and comprising a therapeutically effective amount of a heparinic anticoagulant;
   iii) a mucoadhesive about the periphery of the matrix; and
   iv) a barrier element intermediate the matrix and the mucoadhesive.

* * * * *